United States Patent
Shcherbakov et al.

(10) Patent No.: US 10,206,576 B2
(45) Date of Patent: Feb. 19, 2019

(54) LASER SPECKLE INTERFEROMETRIC SYSTEM AND METHOD FOR MOBILE DEVICES

(71) Applicant: SAMSUNG ELECTRONICS CO., LTD., Suwon-si (KR)

(72) Inventors: Alexander Viacheslavovich Shcherbakov, Moscow region (RU); Alexey Dmitrievich Lantsov, Moscow region (RU)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 231 days.

(21) Appl. No.: 14/849,915

(22) Filed: Sep. 10, 2015

(65) Prior Publication Data

US 2016/0066790 A1  Mar. 10, 2016

(30) Foreign Application Priority Data

Sep. 10, 2014 (RU) .................................. 2014136805
Dec. 15, 2014 (KR) ......................... 10-2014-0180497

(51) Int. Cl.
*G01B 11/02* (2006.01)
*A61B 5/00* (2006.01)
(Continued)

(52) U.S. Cl.
CPC .......... *A61B 5/0059* (2013.01); *A61B 5/0062* (2013.01); *A61B 5/02108* (2013.01);
(Continued)

(58) Field of Classification Search
CPC . A61B 5/0059; A61B 5/0062; A61B 5/02108; A61B 5/02438; A61B 5/6898;
(Continued)

(56) References Cited

U.S. PATENT DOCUMENTS 6,362,873 B1 * 3/2002 Facchini ............ G01B 9/02014
356/35.5
7,925,056 B2    4/2011 Presura et al.
(Continued)

FOREIGN PATENT DOCUMENTS

CA          2824134 A1    7/2012
KR   10-2011-0022132 A    3/2011
(Continued)

OTHER PUBLICATIONS

Takeda et al, "Fourier-transform speckle profilometry: three-dimensional shape measurements of diffuse objects with large height steps and/or spatially isolated surfaces" Dec. 1994, vol. 33, No. 34, Applied Optics.*

(Continued)

*Primary Examiner* — Tarifur R Chowdhury
*Assistant Examiner* — Jonathon Cook
(74) *Attorney, Agent, or Firm* — Sughrue Mion, PLLC (57) ABSTRACT

The laser speckle interferometric system includes a memory for storing a measurement result of a correction parameter and models for matching a result of processing the speckle pattern to the parameters of the object and a processor for stabilizing the speckle pattern detected by controlling a condition for detecting the speckle pattern in real time, processing a time-varying function representing a temporal change in the speckle pattern based on the speckle pattern and the parameters and generating data indicating tested parameters.

29 Claims, 10 Drawing Sheets

(51) Int. Cl.
  *G01B 9/02* (2006.01)
  *A61B 5/024* (2006.01)
  *A61B 5/021* (2006.01)
  *A61B 5/026* (2006.01)
(52) U.S. Cl.
  CPC ........ *A61B 5/02438* (2013.01); *A61B 5/6898* (2013.01); *G01B 9/02094* (2013.01); *G01B 9/02095* (2013.01); *A61B 5/0261* (2013.01)
(58) Field of Classification Search
  CPC .............. A61B 5/0231; G01B 9/02094; G01B 9/02095; G01B 9/02076
  USPC ........................................................ 356/511
  See application file for complete search history.

(56) References Cited

U.S. PATENT DOCUMENTS

| | | | |
|---|---|---|---|
| 2007/0276265 | A1 | 11/2007 | Borgos |
| 2009/0209834 | A1 | 8/2009 | Fine |
| 2010/0226543 | A1* | 9/2010 | Zalevsky ............... A61B 5/024 382/107 |
| 2011/0013002 | A1 | 1/2011 | Thompson et al. |
| 2012/0095354 | A1 | 4/2012 | Dunn et al. |
| 2013/0144137 | A1 | 6/2013 | Zalevsky et al. |
| 2013/0211271 | A1 | 8/2013 | Kang et al. |
| 2015/0323311 | A1* | 11/2015 | Muijs ................... G01B 11/162 356/28.5 |

FOREIGN PATENT DOCUMENTS

| | | |
|---|---|---|
| KR | 10-1065615 B1 | 9/2011 |
| KR | 10-2013-0092849 A | 8/2013 |

OTHER PUBLICATIONS

Yevgeny et al., "Remote estimation of blood pulse pressure via temporal tracking of reflected secondary speckles pattern", Journal of Biomedical Optics, Nov./Dec. 2010, 7 pages total, vol. 15(6).

Kulchin et al., "Correlation method for processing speckles of signals from single-fibre multimode interferometers by using charge-coupled devices", Quantum Electronics, Jan. 12, 2006, 5 pages total.

* cited by examiner

LASER SPECKLE INTERFEROMETRIC SYSTEM AND METHOD FOR MOBILE DEVICES

CROSS-REFERENCE TO RELATED APPLICATIONS

This application claims priority from Russian Patent Application No. 2014136805, filed on Sep. 10, 2014 in the Russian Intellectual Property Office, and Korean Patent Application No. 10-2014-0180497, filed on Dec. 15, 2014, in the Korean Intellectual Property Office, the disclosure of which is incorporated herein by reference in its entirety.

BACKGROUND

1. Field

Methods and apparatuses consistent with one or more exemplary embodiments relate to a laser speckle interferometric system and method, and more particularly, to a laser speckle interferometric system for monitoring a parameter of a biological object by using a mobile device and a laser speckle interferometric method.

2. Description of the Related Art

In laser speckle interferometry, secondary interferometric (i.e., "speckle") patterns are detected and processed. A speckle pattern is formed by scattering of coherent radiation from a rough surface. Laser speckle interferometry has been widely used to monitor engineering parameters and various parameters of biological objects, and the parameters of the biological objects includes variables such as blood pressure, pulse rate, blood flow velocity, and skin condition of a person. Laser speckle interferometry can be performed with non-contact and non-invasive application, high sensitivity, and may be simply implemented.

However, as an existing laser speckle interferometric system is affected by vibration, research into biological parameters using such system has been limited. The vibration problem may be solved by firmly fixing an object under laboratory conditions. In some cases, unfortunately, this solution may be impractical, for example, when parameters of a human body are monitored. Recently, laser speckle interferometry has been used to extract information about pulses and pulse pressure (refer to Yevgeny Beiderman, Israel Horovitz et al., Remote Estimation of Blood Pulse Pressure via Temporal Tracking of Reflected Secondary Speckles Pattern/Journal of Biomedical Optics, 2010, 15(6) 061707), but successful implementation of the laser speckle interferometry uses a tight fixation of a human's arm while extracting the information.

Reference 1 (US 20130144137, METHOD AND SYSTEM FOR NON-INVASIVELY MONITORING BIOLOGICAL OR BIOCHEMICAL PARAMETERS OF INDIVIDUAL, Bar Ilan University, Universitat De Valencia (2012)) discloses a method and system for tracking one or more parameters of a human body. The system includes a controller including an input port for receiving image data, a memory unit, and a processor. Graphic data indicates information collected by a detector in which pixels are arranged and is in the form of a sequence of a speckle pattern formed by scattering, in a portion of the human body, coherent radiation irradiated at predetermined intervals towards the portion. The memory unit stores one or more predetermined models, and the predetermined models include measurable parameters and data representing a relationship between one or more parameters of the human body. The processor is configured to process image data, calculate a spatial correlation function between neighboring speckle patterns through time-series calculation of the spatial correlation function in the form of a time-varying function of at least one parameter of a correlation function, select at least one parameter of a time-varying spatial correlation function in order to determine one or more corresponding parameters of the human body and generate output data corresponding to parameters of the human body to be examined, and apply the at least one selected parameter to one or more preliminary models. The time-varying spatial correlation function represents a temporal change in the speckle pattern. It may be difficult to apply the system and method of reference 1 to a mobile device due to the lack of a vibration reduction device.

Reference 2 (US 20110013002, LASER SPECKLE IMAGING SYSTEMS AND METHODS, Ind Res Ltd, Oliver Bendix Thompson, Michael Kenneth Andrews (2009)) discloses a system and method of measuring perfusion of biological tissues. The disclosed method includes recording images of tissues on which a laser beam is irradiated, providing contrast images of the tissues, determining a power spectrum of radiation scattered from the contrast images, and determining perfusion of the power spectrum. The system includes a processor configured to control a digital video camera, a laser light source, and a camera, produce images with different exposure times, obtain images from the camera, process image data to determine the power spectrum of the radiation, and determine perfusion values of the power spectrum. The above-described method is designed to measure blood flow in tissues of a human body, but may not be sufficient to accurately measure the blood pressure. Also, it may be difficult to apply the method to a mobile device due to the lack of a vibration reduction device.

Reference 3 (U.S. Pat. No. 7,925,056, OPTICAL SPECKLE PATTERN INVESTIGATION, Koninklijke Philips Electronics N.V (2011)) discloses a system and method for medical equipment used for non-invasive in vivo measurement of at least one parameter or a state of a subject having a scattering medium in a target region. The system includes an illumination system, a detection system, and a control system. The illumination system includes at least one light source for generating partially or entirely coherent light to illuminate a region of a human body to cause a light response from the illuminated region. The detection system includes at least one radiation detector for recording a time-varying intensity variation of the light response, and generates data regarding a measurement result of dynamic light scattering. The control system is configured to receive and analyze the measurement result of the dynamic light scattering to determine at least one parameter and generate output data. However, it may be difficult to apply this method to a mobile device due to the lack of a vibration reduction device.

SUMMARY

Exemplary embodiments overcome the above disadvantages and other disadvantages not described above. Also, an exemplary embodiment is not required to overcome the disadvantages described above, and an exemplary embodiment may not overcome any of the problems described above.

Additional aspects will be set forth in part in the description below and, in part, will be apparent from the description, or may be learned by practice of exemplary embodiments.

According to an aspect of an exemplary embodiment, there is provided a laser speckle interferometric system for a mobile device, the laser speckle interferometric system configured to monitor one or more parameters of an object, the system including: an inputter including a laser light source and a detector configured to detect at least one speckle pattern formed by a scattering of a laser beam from the object; a memory configured to store a measurement result of a correction parameter and one or more predetermined patterns for matching a result of processing the speckle pattern to the one or more parameters of the object; and a processor configured to process the speckle pattern, stabilize the detected speckle pattern by controlling a first condition for detecting the speckle pattern in real time, determine a time-varying function for processing the stabilized speckle pattern and representing a temporal change in the speckle pattern according to a change in the one or more parameters of the object, and generate data representing the one or more parameters.

Under the first condition for detecting the speckle pattern, a statistical parameter of a light intensity distribution in the detected speckle pattern may satisfy $I_{av}/I_{max} > 0.15$, wherein $I_{max}$ is a maximum value of a detected light intensity and $I_{av}$ is a mean value of the detected light intensity.

The light intensity distribution may be controlled by adjusting a feedback signal between the laser light source and the detector and an output power of a subsequent laser light source.

Under the first condition for detecting the speckle pattern, a radius R of a detected speckle may satisfy $R0/3 < R < R0$, wherein R0 is a radius of the detected speckle that corresponds to 80% of the detected light intensity.

The size of the detected speckle pattern may be controlled by monitoring a center $(x_c, y_c)$ of the detected speckle pattern, wherein $x_c$ and $y_c$ are coordinates of the center of the detected speckle pattern and are calculated using $$x_c = \sum_{i=1}^{n} x_i I_i(x, y) \Big/ \sum_{i=1}^{n} I_i(x, y)$$

and $$y_c = \sum_{i=1}^{n} y_i I_i(x, y) \Big/ \sum_{i=1}^{n} I_i(x, y)$$

wherein, x and y are coordinates in a detection surface of the detector, n is a total number of pixels in the detection surface of the detector, and I is a value of the light intensity.

The system may include an outputter configured to perform at least one of a function of outputting the data generated by the processor to a display and a function of transmitting the data to another device.

The time-varying function may represent a temporal change in the speckle pattern in a form of a sequence of values of correlation coefficients between respective light intensity distributions of two neighboring speckle patterns.

The time-varying function may represent a temporal change in the speckle pattern in a form of a sequence of values of correlation coefficients between a reference light intensity distribution and a light intensity distribution of the speckle pattern.

The time-varying function may represent a temporal change in the speckle pattern in a form of a sequence of a sum of Fourier Series in each speckle pattern.

The time-varying function may represent a temporal change in the speckle pattern in a form of a sequence of values of a wavelet transform applied to each speckle pattern.

The mobile device may include at least one of a mobile phone and a smart phone.

The mobile device may include at least one of a tablet computer, a personal digital assistant (PDA), and a laptop.

The mobile device may include a watch.

The mobile device may include a display that is configured to be placed on a head of a user.

The mobile device may include a portable media player.

The laser light source and the detector may be disposed in a housing of the mobile device.

The detector may be disposed in a main body of the mobile device, and the laser light source may be disposed in a detachable housing connected to the mobile device.

The outputter may be further configured to output the data to a display of the mobile device.

The outputter may be further configured to output the data to a sound device of the mobile device.

According to an aspect of another exemplary embodiment, there is provided a method of monitoring one or more parameters of an object by using a laser speckle interferometric system for a mobile device, the method including: detecting a speckle pattern as an image, wherein the speckle pattern is formed by irradiating a laser beam onto an object and a scattering of the laser beam from the object; and processing the speckle pattern, wherein the processing of the speckle pattern includes: stabilizing the detected speckle pattern by controlling a first condition for detecting the speckle pattern in real time; determining a time-varying function used to process the stabilized speckle pattern and representing a temporal change in the speckle pattern caused by a change in the one or more parameters of the object; and generating data representing the one or more parameters.

Under the first condition for detecting the speckle pattern, a statistical parameter of a light intensity distribution in the detected speckle pattern may satisfy $I_{av}/I_{max} > 0.15$, wherein $I_{max}$ is a maximum value of a detected light intensity, and $I_{av}$ is a mean value of the detected light intensity.

The light intensity distribution may be controlled by adjusting a feedback signal between a laser light source and a detector and an output power of a subsequent laser light source.

Under the first condition for detecting the speckle pattern, a radius R of a detected speckle may satisfy $R0/3 < R < R0$, wherein R0 is a radius of the detected speckle that corresponds to 80% of the detected light intensity.

A size of the detected speckle pattern may be controlled by monitoring a center of the detected speckle pattern, wherein $x_c$ and $y_c$ are coordinates of the center of the detected speckle pattern and are calculated using $$x_c = \sum_{i=1}^{n} x_i I_i(x, y) \Big/ \sum_{i=1}^{n} I_i(x, y)$$

and $$y_c = \sum_{i=1}^{n} y_i I_i(x, y) \Big/ \sum_{i=1}^{n} I_i(x, y)$$

wherein, x and y are coordinates in a detection surface of the detector, n is a total number of pixels in the detection surface of the detector, and I is a value of the light intensity.

The method may further include at least one of outputting, to a display, data received in a form of the processed speckle pattern and transmitting the data to another device.

In the detecting of the speckle pattern, the detected speckle pattern may be stored as a data file.

The stabilizing of the speckle pattern may include: receiving data from the mobile device; and excluding a speckle pattern from the processing, wherein the excluded speckle pattern may be obtained at a location where the mobile device is not optimized with regard to the object.

The time-varying function may represent a temporal change in the speckle pattern in a form of a sequence of values of correlation coefficients between respective light intensity distributions of two neighboring speckle patterns.

The time-varying function may represent a temporal change in the speckle pattern in a form of a sequence of values of correlation coefficients between a reference light intensity distribution and a current light intensity distribution of the speckle pattern.

The time-varying function may represent a temporal change in the speckle pattern in a form of a sequence of a sum of Fourier Series in each speckle pattern.

The time-varying function may represent a temporal change in the speckle pattern in a form of a sequence of values of a wavelet transform applied to each speckle pattern.

As described above, a portable and mobile device may be used to monitor various parameters of an object, for example, state variables such as the heart rate and blood pressure, according to a laser speckle interferometric method. The portable and mobile device may be, for example, a mobile phone, a smart phone, a watch, a personal digital assistant (PDA), a tablet computer, a portable computer (e.g., a netbook, a laptop, etc.), and the like, but is not limited thereto.

One or more exemplary embodiments may provide a solution to a vibration problem to embody a laser speckle interferometric system based on a mobile device by stabilizing a speckle pattern in a plane of a detector via hardware to provide a feedback between a laser light source and the detector, and/or software to stably control a size, shape, and/or position of a speckle pattern on the plane of the detector.

Furthermore, one or more exemplary embodiments provide a method of processing a speckle pattern, whereby a higher signal to noise ratio than that of an existing method may be obtained.

BRIEF DESCRIPTION OF THE DRAWINGS

These and/or other aspects will become apparent and more readily appreciated from the following description of one or more exemplary embodiments, taken in conjunction with the accompanying drawings in which.

DETAILED DESCRIPTION

Reference will now be made to exemplary embodiments, examples of which are illustrated in the accompanying drawings, wherein like reference numerals refer to like elements throughout. The exemplary embodiments may, however, be embodied in many different forms and should not be construed as being limited to one or more exemplary embodiments set forth herein. Like reference numerals in the drawings denote like elements, and sizes of components in the drawings may be exaggerated for convenience of explanation. Expressions such as "at least one of," when preceding a list of elements, modify the entire list of elements and do not modify the individual elements of the list.

A laser speckle interferometric system may include an information input unit (e.g., inputter) including a laser light source and a detector; a memory unit (e.g., memory) storing research model data, correction data, and a measurement result; and a processing unit (e.g., processor) for performing speckle stabilization and speckle processing. Also, the laser speckle interferometric system may further include an output unit (e.g., outputter) for displaying the measurement result to a user and/or transmitting received data to another device. A blood pressure and pulse rate of a person may be obtained according to a laser speckle interferometric method.

A laser beam emitted from the laser light source is scattered on a skin surface of a wrist of a person, and a speckle pattern formed by scattering of coherent light is detected by the detector and then recorded. Pulsation in arteries causes a skin movement that affects the detected speckle pattern. To detect pulsation having a signal to noise ratio that is high enough to perform accurate measurement, the influence of a vibration caused by a displacement between the mobile device and an object under examination may be removed. The detection of pulsation may be achieved by monitoring, in real time, parameters used to detect optimal conditions [Kulchin Yu. N., Vitrik O. B., Lantsov A. D., Correlation Method for Processing Speckles of Signals from Single-Fiber Multimode Interferometers by using Charge-Coupled Devices, Quantum Electron, (2006), 36(4), 339-342]. The parameters may be a statistical parameter of a light intensity distribution in the detected speckle pattern satisfying $I_{av}/I_{max} > 0.15$ (where, $I_{max}$ is a maximum value of a detected light intensity, and $I_{av}$ is a mean value of the detected light intensity) and a radius of a detected speckle within a range of $R0/3 < R < R0$ (where, R0 is a radius of the detected speckle that corresponds to 80% of the entire detected light intensity). The light intensity distribution is controlled by adjusting a feedback signal between the light source and the detector and an output of a subsequent light source. An optimal (i.e., acceptable) size of the detected speckle pattern may be controlled by monitoring a center $(x_c, y_c)$ of the detected speckle pattern, wherein $x_c$ and $y_c$ are the coordinates of the center of the speckle pattern and are calculated according to Equations 1 and 2 below.

$$x_c = \sum_{i=1}^{n} x_i I_i(x, y) \bigg/ \sum_{i=1}^{n} I_i(x, y) \quad \text{[Equation 1]}$$

and $$y_c = \sum_{i=1}^{n} y_i I_i(x, y) \bigg/ \sum_{i=1}^{n} I_i(x, y) \quad \text{[Equation 2]}$$

wherein, x and y are coordinates on a detection surface of the detector, n is a total number of pixels in the detection surface of the detector, and I is a value of a light intensity.

A stabilized speckle pattern may be used to determine a time-varying function that is displayed as a sum of all components obtained from Fourier Series applied to respective images of the detected speckle pattern. The time-varying function represents a temporal change in the speckle pattern and may include information regarding the parameters of an object.

The determined time-varying function corresponds to time dependence of the blood pressure at an artery wall, and a repetition frequency of a maximum value of the time-varying function corresponds to the heart beats of a person. A shape of the time-varying function, that is, an envelope, may be determined based on a temporal shape of the blood pressure, among other physiological parameters. The number of detected peaks of the time-varying function may be counted to determine a size of a pulsation for a predetermined time, for example, 1 minute. Before the laser speckle interferometric system and method for the mobile device is used, the entire system may be corrected, that is, the entire system may be calibrated by recording several periods of a pulse wave and to store the recorded periods of the pulse wave in the memory unit to thereby determine a value of the blood pressure. Almost immediately before or after the above procedure, the blood pressure may be measured via an existing sphygmomanometer and then an obtained result may be recorded in the memory unit. Therefore, the memory unit may store a shape of the pulse wave and the blood pressure values corresponding thereto. After a correction process, there is no need to use the existing sphygmomanometer, and the blood pressure may be measured any time via the laser speckle interferometric system and method.

Current values of the blood pressure may be calculated as follows. The processing unit calculates proportional coefficients to determine a difference between a current shape of a blood wave and the pulse wave stored in the memory unit. Then, the calculated proportional coefficients and a corrected value of the blood pressure are multiplied. A result value of the blood pressure is displayed to a user and may be selectively transmitted to another device in a wireless manner.

Figure 1:
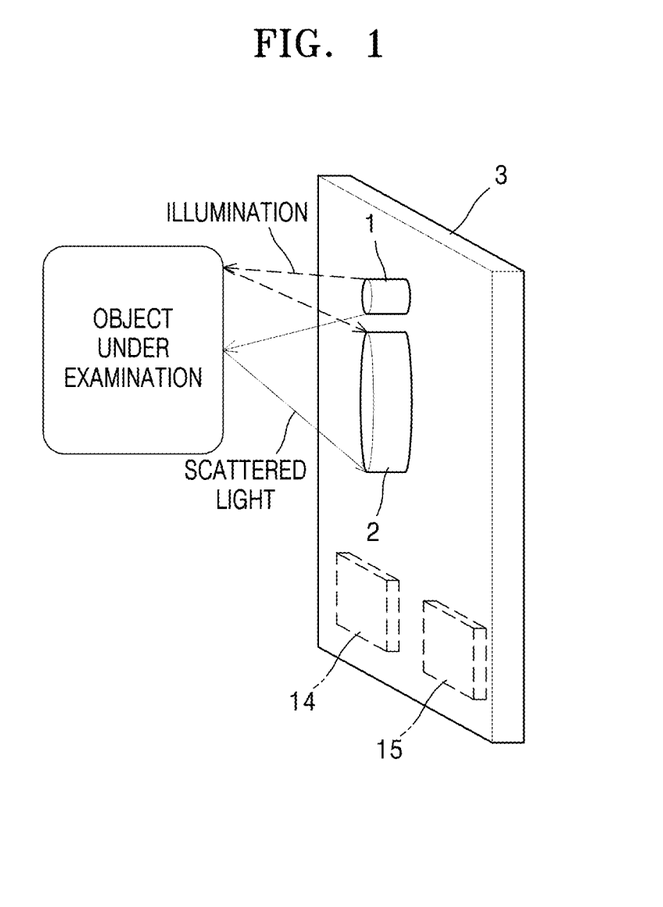
FIG. 1 illustrates a laser speckle interferometric system for a mobile device, according to an exemplary embodiment.

FIG. 1 illustrates a laser speckle interferometric system for a mobile device according to an exemplary embodiment. The laser speckle interferometric system of FIG. 1 may include a laser light source 1, a detector 2, a processing unit 14, and a memory unit 15.

The laser light source 1 emits a laser beam having coherence. The laser light source 1 may be, for example, a semiconductor laser diode. The detector 2 may capture a speckle pattern image and may be, for example, an image sensor or a camera including an image sensor. The processing unit 14 and the memory unit 15 may be integrated into a main body 3 of the mobile device such that vibrations generated by the displacement between the laser light source 1 and the detector 2 are dampened.

Figure 3:
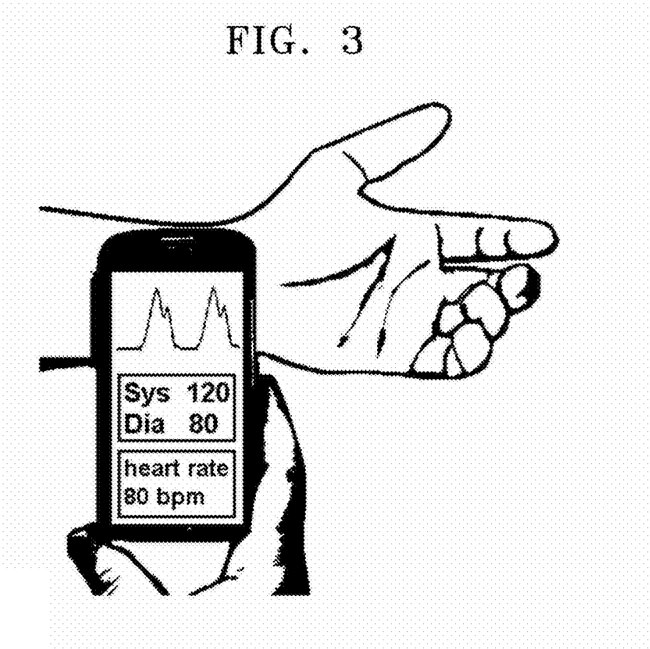
FIG. 3 illustrates a laser speckle interferometric system configured to measure a blood pressure and a heart rate, according to an exemplary embodiment.

Also, the laser speckle interferometric system may further include a display for displaying a pulse rate or blood pressure (refer to FIG. 3). The display is an example of the output unit. As another example, the output unit of the laser speckle interferometric system may include a speaker for outputting the pulse rate or blood pressure as a sound signal or a voice signal or a communication unit (e.g., communicator) for transmitting data to another device in a wired or wireless manner.

The mobile device may be, for example, a mobile phone or a smart phone, a tablet computer, a personal digital assistant (PDA), a laptop, a portable media player, a watch, or a display placed on a user's head.

Figure 2:
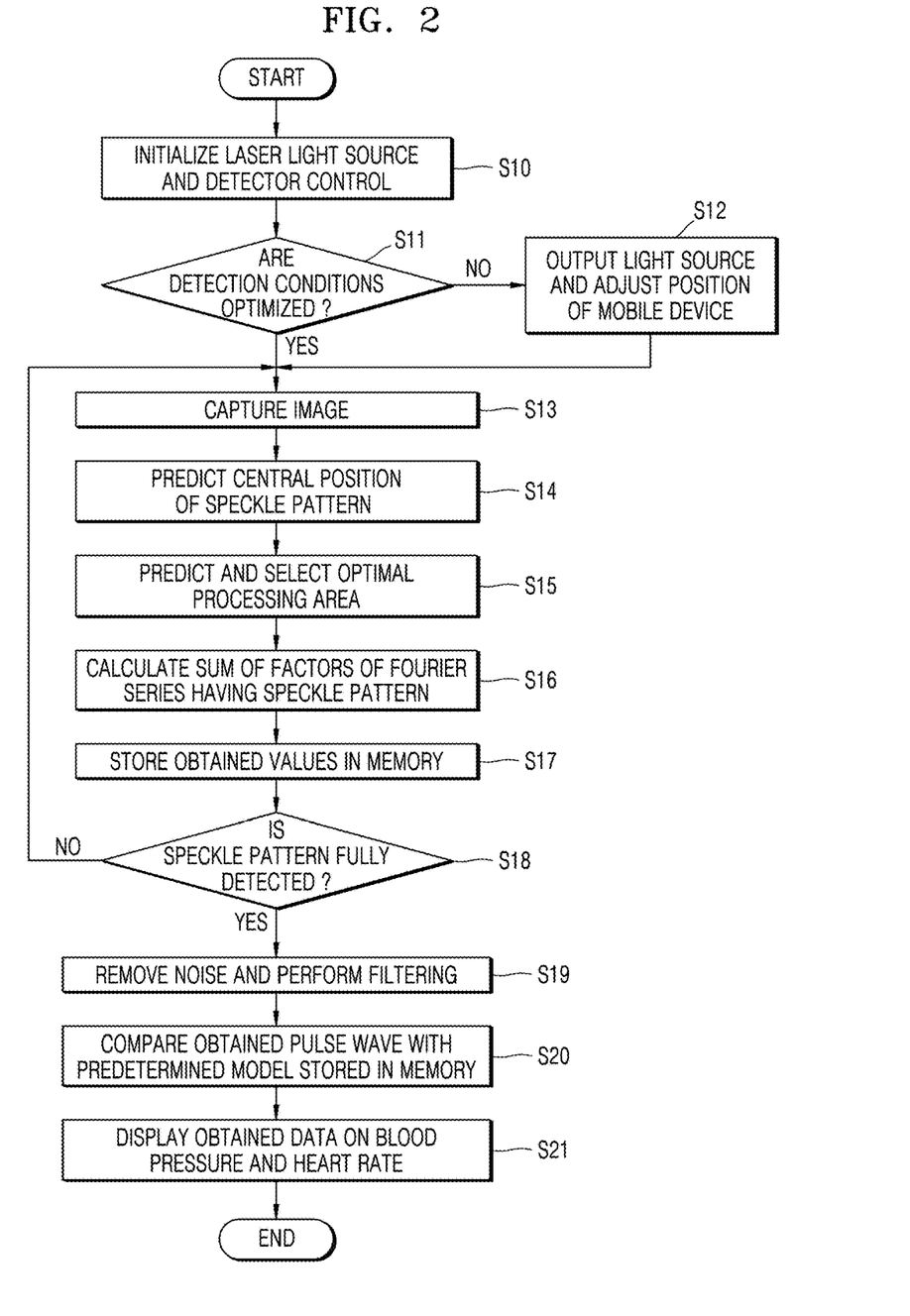
FIG. 2 illustrates a flowchart of a laser speckle interferometric method for a mobile device, according to an exemplary embodiment.

FIG. 2 illustrates a flowchart of a laser speckle interferometric method for a mobile device, according to an exemplary embodiment. As described with reference to FIG. 2, the laser speckle interferometric system performs processes according to the laser speckle interferometric method.

FIG. 3 illustrates a laser speckle interferometric system configured to measure a blood pressure and a heart rate, according to an exemplary embodiment. FIG. 3 illustrates an initial position of the laser speckle interferometric system configured to measure parameters of a human body, that is, a blood pressure and a heart rate. As illustrated in FIG. 3, in order to minimize a vibration influence during measurement of the parameters, the mobile device is positioned on a surface of an object. The object of FIG. 3 is a wrist of a person.

In operation S10, the control of laser light source 1 and the detector 2 is initialized. After initialization, the laser light source 1 of the laser speckle interferometric system emits a laser beam onto a region of interest (ROI) of the object. The laser beam is scattered in the region of interest and is detected by the detector.

Figure 4:
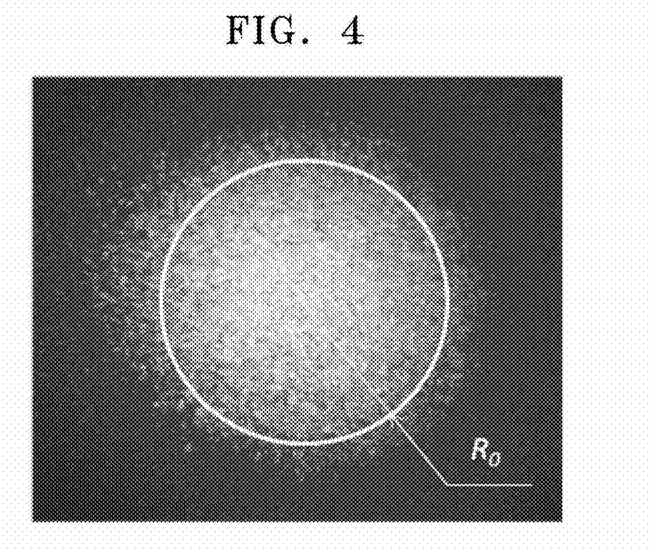
FIG. 4 illustrates a speckle pattern detected to be used in a laser speckle interferometric system for a mobile device, according to an exemplary embodiment.

FIG. 4 illustrates an example of a speckle pattern that is detected and used in a laser speckle interferometric system for a mobile device. The processing unit 14 analyzes an illumination value on the detector and provides feedback signals to the laser light source 1 to adjust output power in such a way that optimal conditions for detecting the laser beam are satisfied. The optimal conditions may be as follows: a statistical parameter of light intensity distribution in the detected speckle pattern satisfying $I_{av}/I_{max} > 0.15$ (for which $I_{max}$ is a maximum value of a detected light intensity, and $I_{av}$ is a mean value of the detected light intensity); and a radius of a detected speckle within a range of $R0/3 < R < R0$ (for which R0 is a radius of the detected speckle that corresponds to 80% of the entire detected light intensity). Under the optimal conditions, a linear regime of a speckle pattern field may be obtained. After a determination as to whether detection conditions are optimized is made in operation S11, if the detection conditions are not optimized, an output of the laser light source 1 and a position of the mobile device may be adjusted in operation S12.

After an initial setting is completed, stabilization and measurement of the speckle pattern are simultaneously performed. An image of light emitted from the laser light source 1 and scattered on a subject under examination is captured in operation S13. Then, a central position of the speckle pattern is predicted based on the captured image in operation S14. Also, an optimal processing area is predicted and then selected in operation S15. The stabilization of the speckle pattern may be achieved by monitoring the optimal conditions for detecting the speckle pattern and the central point of the speckle pattern at the same time. The coordinates of the center of the speckle pattern, that is, $x_c$ and $y_c$, are calculated based on the above Equation 1.

The processing unit 14 performs image processing in real time and may determine not to store each frame in the memory unit 15. This may improve the performance of the entire system. The processing unit 14 performs a Fourier transform on each frame and determines a set of spatial frequencies from the image in operation S16. The transformed frames of the image are characterized by a set of spatial frequencies, and a sum of all components corresponds to the time-varying function at a predetermined point in time. The time-varying function represents a temporal change in the speckle pattern in the form of a sequence of a sum of Fourier Series. However, the time-varying function is not limited thereto and may represent a temporal change in the speckle pattern in the form of a sequence of values of correlation coefficients between a reference intensity distribution and the light intensity distribution at the speckle pattern or in the form of a sequence of values of wavelet transform coefficients applied to each speckle pattern.

Then, noise is removed by filtering in operation S19.

Obtained values are stored in the memory unit 15 in operation S17. In operation S18, if the speckle pattern is not sufficiently detected, the above operations are repeated starting from operation S13.

Figure 6:
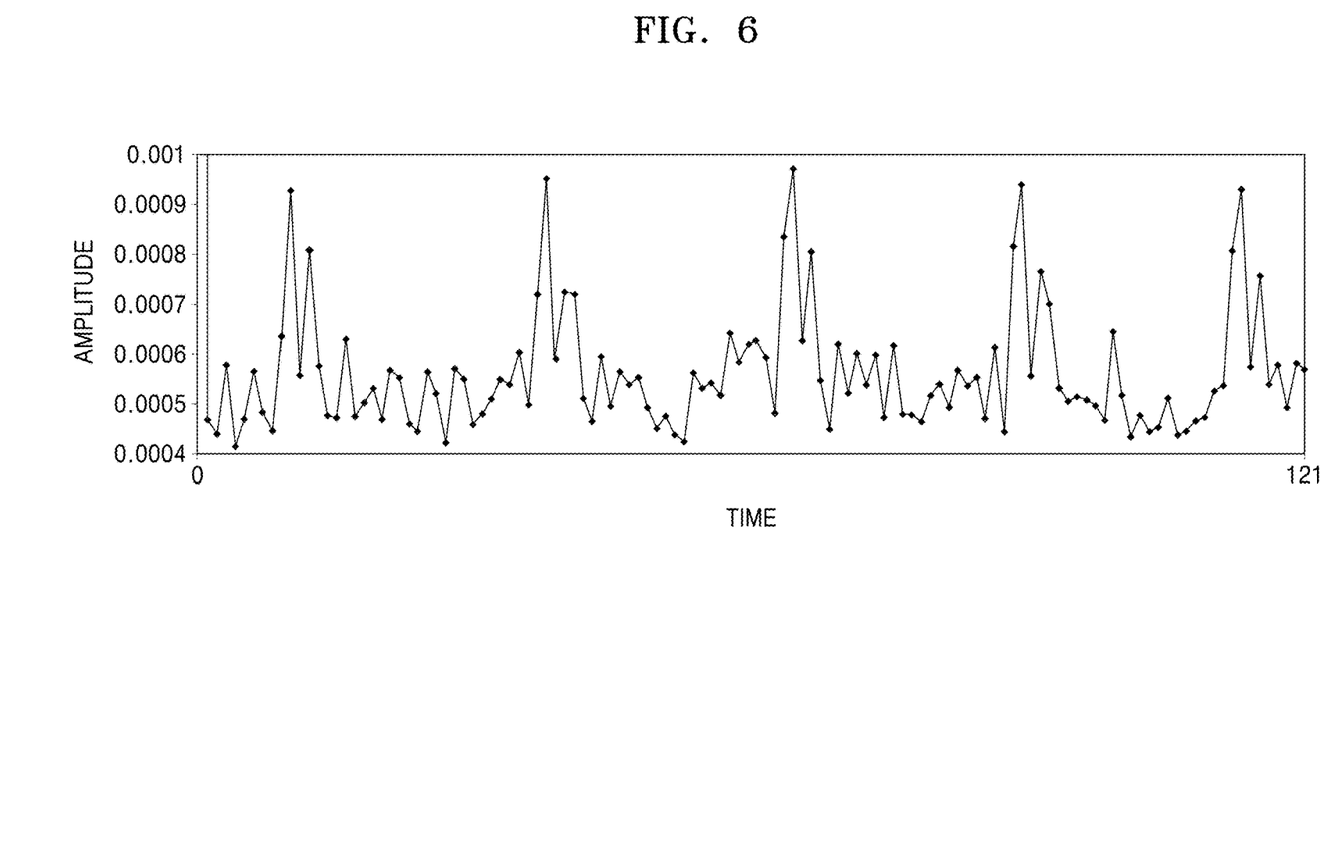
FIG. 6 illustrates a graph of pulsation detected by a laser speckle interferometric system for a mobile device, according to a laser speckle contrast analysis (LASCA) method, according to an exemplary embodiment.
Figure 7:
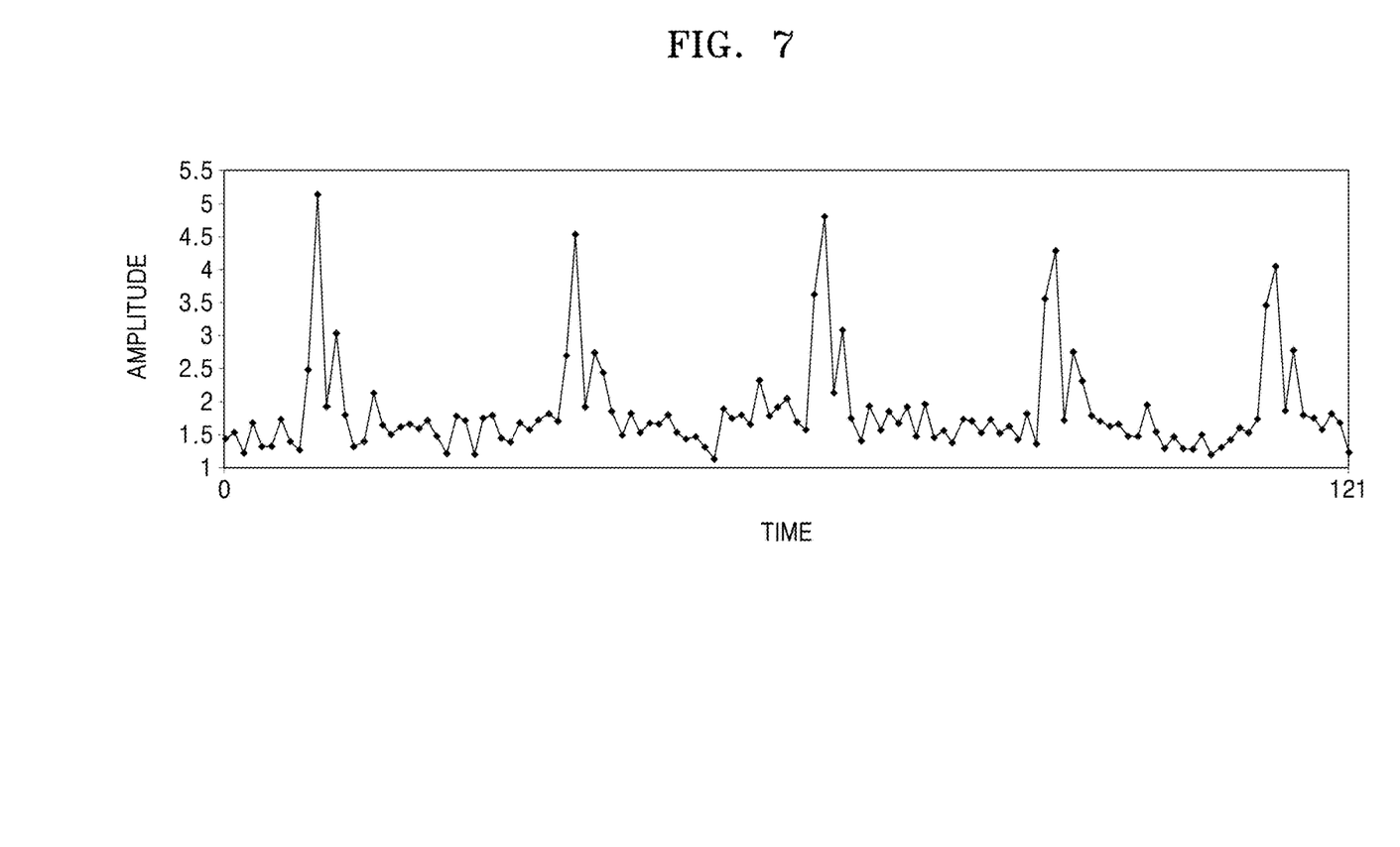
FIG. 7 illustrates a graph of pulsation detected by a laser speckle interferometric system according to a Fourier transform, according to an exemplary embodiment.

FIG. 6 illustrates a graph of a pulsation detected by the laser speckle interferometric system for a mobile device, via a laser speckle contrast analysis (LASCA) method, according to an exemplary embodiment. FIG. 6 illustrates a time dependence obtained from the speckle pattern formed by scattering of light from a skin surface of a wrist. FIG. 7 illustrates a graph of a pulsation detected by the laser speckle interferometric system according to Fourier transform. Upon comparing FIGS. 6 and 7, a result obtained using an algorithm based on the Fourier transform has a similar time dependence to the time dependence obtained using the LASCA method. The above-described method allows a user to obtain peaks corresponding to pulses of a person, the pulses having a high signal to noise ratio, and the high signal to noise ratio results in a relatively large contrast of the peaks with respect to a background signal.

Figure 5:
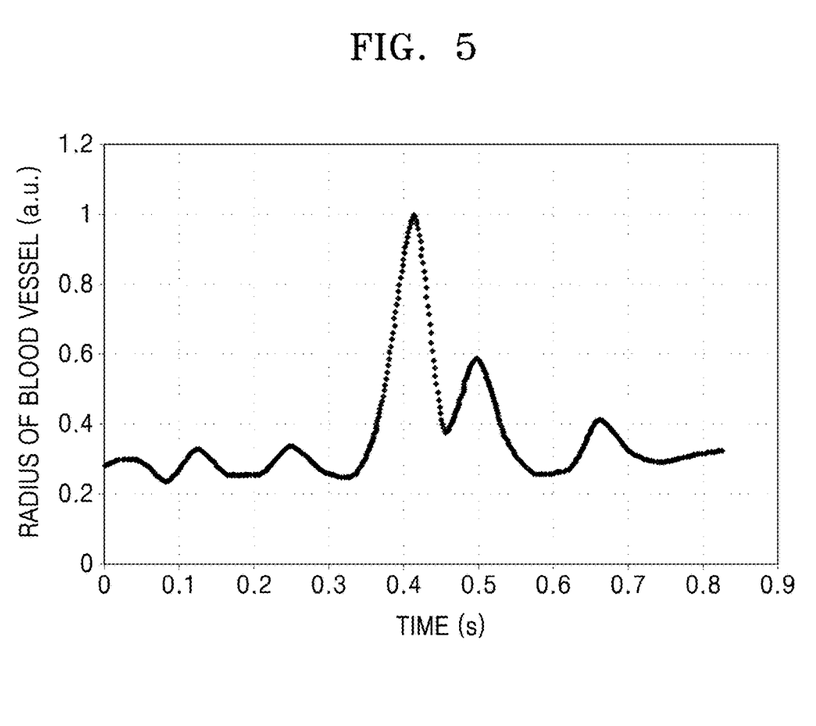
FIG. 5 illustrates a graph of pulsation detected by a laser speckle interferometric system for a mobile device, according to an exemplary embodiment.

In operation S20, one or more models are used to describe a relationship between a single pulse wave and the blood pressure corresponding thereto. The single pulse wave is obtained during one cardiac cycle and is stored in the memory unit 15. FIG. 5 illustrates a graph of a pulsation detected by the laser speckle interferometric system for a mobile device, according to an exemplary embodiment. An exemplary pulse wave of FIG. 5 is obtained during one cardiac cycle and is stored in the memory unit 15. The processing unit 14 may restore a current value of the blood pressure by comparing the pulse wave stored in the memory unit 15 with a measured pulse wave.

An obtained value of the blood pressure may be displayed on a display of the mobile device in operation S21. The obtained value of the blood pressure may be stored in the memory unit 15 of the mobile device and may be transmitted to another device in a wireless manner or another manner well known to one of ordinary skill in the art.

Figure 8:
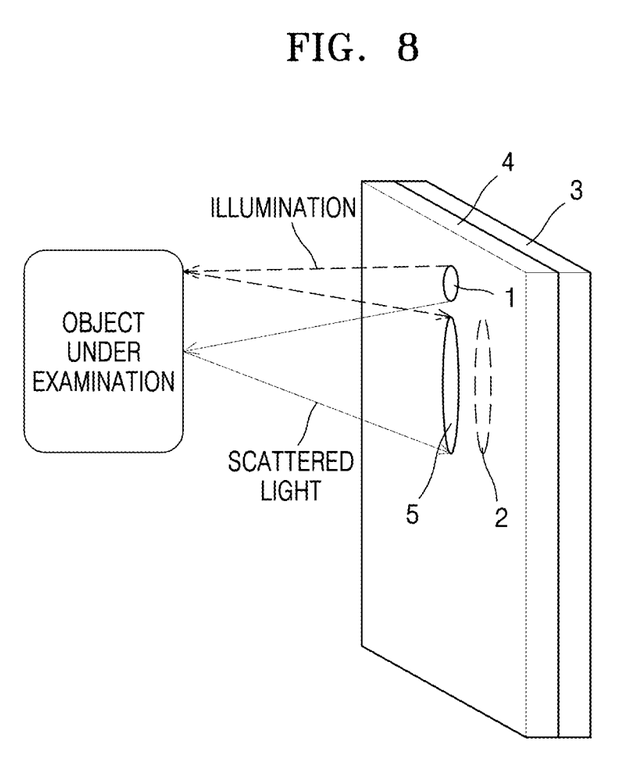
FIG. 8 illustrates a laser speckle interferometric system for a mobile device, according to another exemplary embodiment.

FIG. 8 illustrates a laser speckle interferometric system for a mobile device, according to another exemplary embodiment. Referring to FIG. 8, the laser speckle interferometric system may include the laser light source 1, the detector 2, a main body 3 of the mobile device, a detachable housing 4, and an aperture 5. The laser light source 1 may be arranged in the detachable housing 4 that is detachably connected to the mobile device. The detector 2 may be a camera of the mobile device. As another example, the detector 2 may be arranged in the detachable housing. The aperture 5 is arranged in the detachable housing. The detector 2 detects scattered light having a speckle pattern through the aperture 5. The laser speckle interferometric system according to an exemplary embodiment may be placed in an arbitrary mobile device that may be connected to the detachable housing 4. For example, the mobile device may be a mobile phone, a smart phone, a tablet computer, a PDA, a laptop, or a portable media player. Alternatively, the mobile device may be a watch or a display placed on a user's head.

Figure 9:
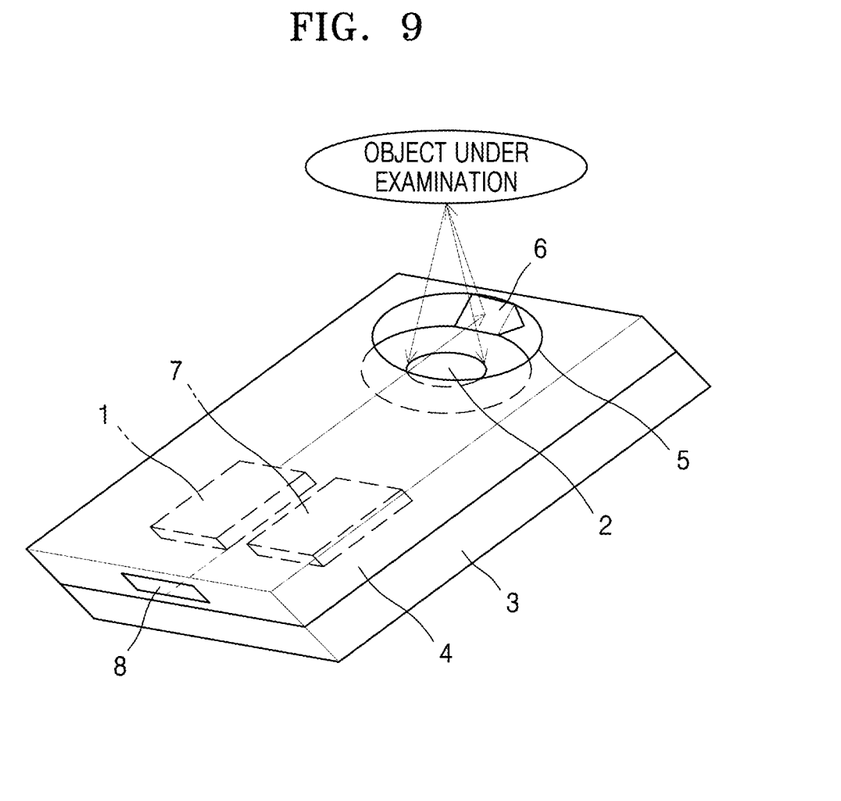
FIG. 9 illustrates a laser speckle interferometric system for a mobile device, according to another exemplary embodiment.

FIG. 9 illustrates a laser speckle interferometric system for a mobile device, according to another exemplary embodiment. Referring to FIG. 9, the laser speckle interferometric system may include the laser light source 1, the detector 2, the main body 3 of the mobile device, the detachable housing 4, the aperture 5, a prism minor 6, a power device 7, and an operation button 8. The laser light source 1 may be placed in the detachable housing 4 that is detachably connected to the mobile device. The aperture 5 is arranged in the detachable housing. The prism mirror 6 is placed on a side of the aperture 5 and changes an optical path of a laser beam emitted from the laser light source 1 in such a manner that the laser beam is emitted toward the object under examination. The detector 2 detects scattered light having a speckle pattern through the aperture 5. The operation button 8 is used to turn on or off the laser speckle interferometric system. The laser speckle interferometric system may be arranged in a mobile device that may be connected to the detachable housing 4. For example, the mobile device may be a mobile phone, a smart phone, a tablet computer, a PDA, a laptop, a portable media player, a watch, or a display resting on a user's head.

Figure 10:
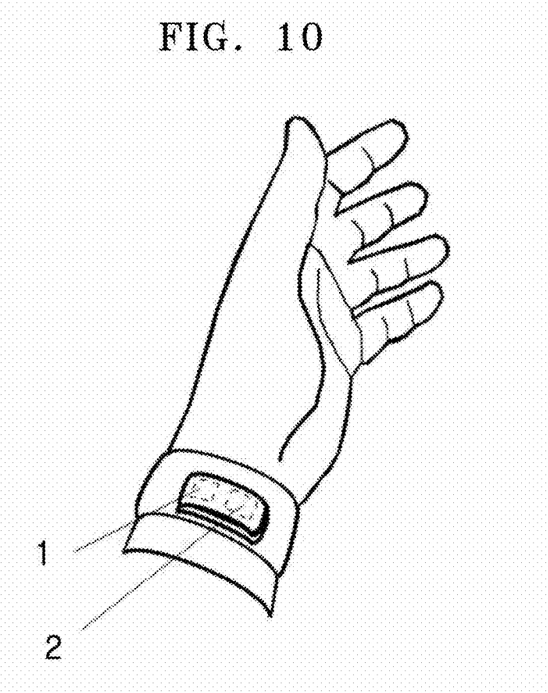
FIG. 10 illustrates a laser speckle interferometric system for a mobile device, according to another exemplary embodiment.
Figure 11:
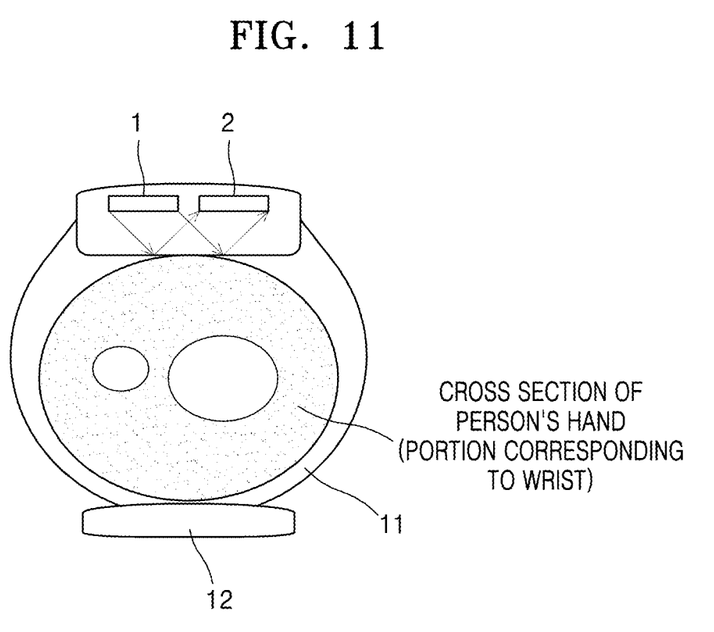
FIG. 11 illustrates a side view of a laser speckle interferometric system for a mobile device, according to another exemplary embodiment.

FIG. 10 illustrates a laser speckle interferometric system for a mobile device, according to another exemplary embodiment, and FIG. 11 illustrates a side view of the laser speckle interferometric system of FIG. 10 for a mobile device, according to another exemplary embodiment.

Referring to FIGS. 10 and 11, the laser speckle interferometric system may include the laser light source 1, the detector 2, a strap fixer 12, and wrist straps 11 worn on a wrist of the user. The laser speckle interferometric system according to an embodiment may use a mobile device worn on a wrist of the user, for example, a watch, and may be used to track temporal parameters of a human body, for example, the pulse rate, blood pressure, and the like.

Figure 12:
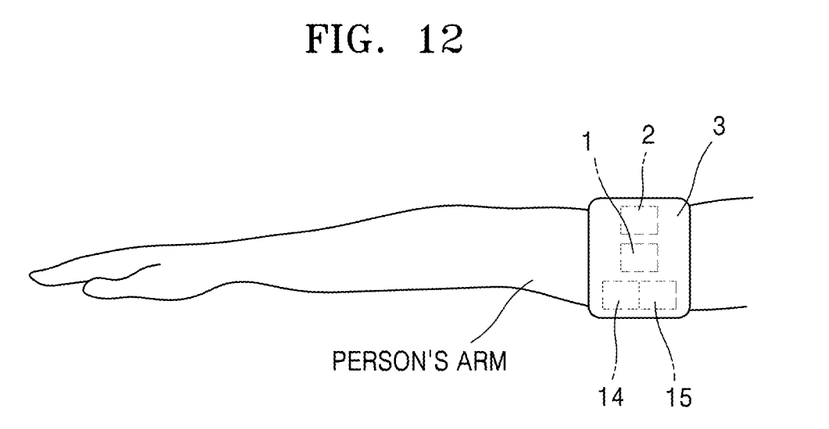
FIG. 12 illustrates a laser speckle interferometric system for a mobile device, according to another exemplary embodiment.

FIG. 12 illustrates a laser speckle interferometric system for a mobile device, according to another exemplary embodiment. Referring to FIG. 12, the laser speckle interferometric system may include the laser light source 1, the detector 2, main body 3, a strap fixer 12, the processing unit 14, and the memory unit 15. The strap fixer 12 may be an arm strap worn on an arm of the user. The laser speckle interferometric system may be applied to a mobile device of a cuff type to be worn on an arm of the user. For example, the laser speckle interferometric system according to an exemplary embodiment may be used when a brachial artery is used for measurement and correction of vital signs such as the blood pressure and heart rate.

The laser speckle interferometric system and method according to one or more exemplary embodiments may be applied to a mobile device used to monitor biological parameters of a human or an animal. It may be understood by one of ordinary skill in the art that the laser speckle interferometric system and method may be used in security and medical system fields. The laser speckle interferometric system and method according to the one or more exemplary embodiments may have high mobility and portability because one or more parameters of a human may be tracked without using a specially designed device.

The laser speckle interferometric system and method according to one or more exemplary embodiments may be embodied by hardware, software, firm ware, an integrated circuit, a microprocessor, a memory device, a computer-readable recording medium, and any combination thereof.

A method of monitoring one or more parameters of an object by using the laser speckle interferometric system for a mobile device may be written as a program executable by a computer and may be implemented in a general-use digital computer using a non-transitory computer-readable recording medium. The non-transitory computer-readable recording medium includes magnetic storage media (e.g., ROM, RAM, USBs, floppy disks, hard disks, etc.), optical recording media (e.g., CD-ROMs, or DVDs), and PC interfaces (e.g., PCI, PCI-express, Wi-fi, etc.), etc.

It should be understood that exemplary embodiments described herein should be considered in a descriptive sense only and not for purposes of limitation. Descriptions of features or aspects within an exemplary embodiment should be considered as available for other similar features or aspects in other exemplary embodiments.

While one or more exemplary embodiments have been described with reference to the figures, it should be understood by those of ordinary skill in the art that various changes in form and details may be made therein without departing from the spirit and scope as defined by the following claims.

What is claimed is:

1. A laser speckle interferometric system for a mobile device, the laser speckle interferometric system configured to monitor one or more parameters of an object, the system comprising:
    a laser light source configured to emit a laser beam to the object;
    a detector configured to receive the laser beam that is emitted to and scattered by the object, and detect at least one speckle pattern from the received laser beam, said speckle pattern being representative of a first biological activity of the object;
    a memory configured to store a measurement result of a correction parameter and one or more predetermined patterns for matching a result of processing the speckle pattern to the one or more parameters of the object;
    a processor configured to process the speckle pattern of the first biological activity that is detected from the received laser beam; and
    a controller configured to control a light intensity distribution and a radius of the speckle pattern in real time so that a ratio of an average light intensity to a maximum light intensity of the speckle pattern is greater than a predetermined value and the radius of the detected speckle pattern is within a predetermined range by adjusting a feedback signal between the laser light source and the detector and an output power of a subsequent laser light source,
    wherein
    the processor stabilizes the detected speckle pattern, while the speckle pattern is being measured, by monitoring a center of the speckle pattern,
    determines a time-varying function for processing the stabilized speckle pattern and representing a temporal change in the speckle pattern of the first biological activity according to a change in the one or more parameters of the object to ascertain a second biological activity of the object in which vibrational components of the object are removed, generates data representing the one or more parameters corresponding to the second biological activity of the object, and displays the data representing the one or more parameters in numerical form to a user.

2. The laser speckle interferometric system of claim 1, wherein the predetermined value is 0.15.

3. The laser speckle interferometric system of claim 1, wherein the predetermined range is from $R_0/3$ to $R_0$, and $R_0$ is 80% of an entire detected light intensity.

4. The laser speckle interferometric system of claim 3, wherein the size of the detected speckle pattern is controlled by monitoring the center $(x_c, y_c)$ of the detected speckle pattern, wherein $x_c$ and $y_c$ are coordinates of the center of the detected speckle pattern and are calculated using $$x_c = \sum_{i=1}^{n} x_i I_i(x, y) \bigg/ \sum_{i=1}^{n} I_i(x, y)$$

and $$y_c = \sum_{i=1}^{n} y_i I_i(x, y) \bigg/ \sum_{i=1}^{n} I_i(x, y)$$

wherein, x and y are coordinates in a detection surface of the detector, n is a total number of pixels in the detection surface of the detector, and I is a value of the detected light intensity.

5. The laser speckle interferometric system of claim 1, further comprising an outputter configured to perform at least one of a function of outputting the data generated by the processor to a display and a function of transmitting the data to another device.

6. The laser speckle interferometric system of claim 5, wherein the outputter is further configured to output the data to a display of the mobile device.

7. The laser speckle interferometric system of claim 5, wherein the outputter is further configured to output the data to a sound device of the mobile device.

8. The laser speckle interferometric system of claim 1, wherein the time-varying function represents a temporal change in the speckle pattern in a form of a sequence of values of correlation coefficients between respective light intensity distributions of two neighboring speckle patterns.

9. The laser speckle interferometric system of claim 1, wherein the time-varying function represents a temporal change in the speckle pattern in a form of a sequence of values of correlation coefficients between a reference light intensity distribution and a light intensity distribution of the speckle pattern.

10. The laser speckle interferometric system of claim 1, wherein the time-varying function represents a temporal change in the speckle pattern in a form of a sequence of a sum of Fourier Series in each speckle pattern.

11. The laser speckle interferometric system of claim 1, wherein the time-varying function represents a temporal change in the speckle pattern in a form of a sequence of values of a wavelet transform applied to each speckle pattern.

12. The laser speckle interferometric system of claim 1, wherein the mobile device comprises at least one of a mobile phone and a smart phone.

13. The laser speckle interferometric system of claim 1, wherein the mobile device comprises at least one of a tablet computer, a personal digital assistant (PDA), and a laptop.

14. The laser speckle interferometric system of claim 1, wherein the mobile device comprises a watch.

15. The laser speckle interferometric system of claim 1, wherein the mobile device comprises a display that is configured to be placed on a head of the user.

16. The laser speckle interferometric system of claim 1, wherein the mobile device comprises a portable media player.

17. The laser speckle interferometric system of claim 1, wherein the laser light source and the detector are disposed in a housing of the mobile device.

18. The laser speckle interferometric system of claim 1, wherein the detector is disposed in a main body of the mobile device, and
the laser light source is disposed in a detachable housing connected to the mobile device.

19. A method of monitoring one or more parameters of an object by using a laser speckle interferometric system for a mobile device, the method comprising:
emitting a laser beam to the object;
receiving the laser beam that is emitted to and scattered by the object;
detecting a speckle pattern as an image from the received laser beam, said speckle pattern being representative of a first biological activity of the object;
processing the speckle pattern of the first biological activity that is detected from the received laser beam; and
controlling a light intensity distribution and a radius of the speckle pattern in real time so that a ratio of an average light intensity to a maximum light intensity of the speckle pattern is greater than a predetermined value and the radius of the detected speckle pattern is within a predetermined range by adjusting a feedback signal between the laser light source and a detector and an output power of a subsequent laser light source,
wherein the processing of the speckle pattern comprises:
stabilizing, while the speckle pattern is being measured, the speckle pattern by monitoring a center of the speckle pattern and controlling a radius of the speckle pattern;
determining a time-varying function used to process the stabilized speckle pattern and representing a temporal change in the speckle pattern of the first biological activity according to a change in the one or more parameters of the object to ascertain a second biological activity of the object in which vibrational components of the object are removed;
generating data representing the one or more parameters corresponding to the second biological activity of the object; and
displaying the data representing the one or more parameters in numerical form to a user.

20. The method of claim 19, wherein the predetermined value is 0.15.

21. The method of claim 19, wherein, the predetermined range is from $R_0/3$ to $R_0$, and $R_0$ is 80% of an entire detected light intensity.

22. The method of claim 21, wherein a size of the detected speckle pattern is controlled by monitoring the center of the detected speckle pattern, wherein $x_c$ and $y_c$ are coordinates of the center of the detected speckle pattern and are calculated using $$x_c = \sum_{i=1}^{n} x_i I_i(x, y) \bigg/ \sum_{i=1}^{n} I_i(x, y)$$

and $$y_c = \sum_{i=1}^{n} y_i I_i(x, y) \bigg/ \sum_{i=1}^{n} I_i(x, y)$$

wherein, x and y are coordinates in a detection surface of a detector that detects the speckle pattern, n is a total number of pixels in the detection surface of the detector, and I is a value of the light intensity.

23. The method of claim 19, further comprising at least one of outputting, to a display, data received in a form of the processed speckle pattern and transmitting the data to another device.

24. The method of claim 19, wherein, in the detecting of the speckle pattern, the detected speckle pattern is stored as a data file.

25. The method of claim 19, wherein the stabilizing of the speckle pattern comprises:
receiving data from the mobile device; and
excluding a speckle pattern from the processing, wherein the excluded speckle pattern is obtained at a location where the mobile device is not optimized with regard to the object.

26. The method of claim 19, wherein the time-varying function represents a temporal change in the speckle pattern in a form of a sequence of values of correlation coefficients between respective light intensity distributions of two neighboring speckle patterns.

27. The method of claim 19, wherein the time-varying function represents a temporal change in the speckle pattern in a form of a sequence of values of correlation coefficients between a reference light intensity distribution and a current light intensity distribution of the speckle pattern.

28. The method of claim 19, wherein the time-varying function represents a temporal change in the speckle pattern in a form of a sequence of a sum of Fourier Series in each speckle pattern.

29. The method of claim 19, wherein the time-varying function represents a temporal change in the speckle pattern in a form of a sequence of values of a wavelet transform applied to each speckle pattern.

* * * * *